United States Patent
Heitmeier et al.

(10) Patent No.: US 10,076,604 B2
(45) Date of Patent: Sep. 18, 2018

(54) PUMP FOR MEDICAL PURPOSES

(71) Applicant: B. BRAUN MELSUNGEN AG, Melsungen (DE)

(72) Inventors: Rolf Heitmeier, Baunatal (DE); Dominik Niedenzu, Kassel (DE); Berthold Wolfram, Melsungen (DE); Matthias Schwalm, Schwalmstadt (DE); Heiko Rosenkranz, Knuellwald (DE); Juergen Steger, Koerle (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 22 days.

(21) Appl. No.: 14/653,167

(22) PCT Filed: Dec. 23, 2013

(86) PCT No.: PCT/EP2013/077950
§ 371 (c)(1),
(2) Date: Jun. 17, 2015

(87) PCT Pub. No.: WO2014/102259
PCT Pub. Date: Jul. 3, 2014

(65) Prior Publication Data
US 2015/0328399 A1    Nov. 19, 2015

(30) Foreign Application Priority Data

Dec. 24, 2012 (DE) .................. 10 2012 113 087

(51) Int. Cl.
*A61M 31/00* (2006.01)
*A61M 5/142* (2006.01)
*A61M 5/145* (2006.01)

(52) U.S. Cl.
CPC .... *A61M 5/14224* (2013.01); *A61M 5/14593* (2013.01); *A61M 5/14228* (2013.01); *A61M 2005/14513* (2013.01)

(58) Field of Classification Search
CPC .......... A61M 5/14224; A61M 5/14993; A61M 5/14228
(Continued)

(56) References Cited

U.S. PATENT DOCUMENTS 3,895,741 A    7/1975 Nugent
4,382,753 A    5/1983 Archibald
(Continued)

FOREIGN PATENT DOCUMENTS

CN    101918054    12/2010
CN    102036702    4/2011
(Continued)

OTHER PUBLICATIONS

International Search Report for PCT/EP2013/077950 dated May 27, 2014.
(Continued)

*Primary Examiner* — Edelmira Bosques
(74) *Attorney, Agent, or Firm* — RatnerPrestia

(57) ABSTRACT

A medical fluid pump, comprising a first, inner fluid system including a motor-driven suction/pressure unit and a first fluid pressure chamber which can be filled with fluid and emptied by the suction/pressure unit, and a second, outer fluid system including a second fluid pressure chamber which is coupled to the first pressure chamber in a pressure- and/or volume-dynamic manner via a movable separating wall and which is alternately coupled—via a valve means of the second fluid system—to a suction line and pressure line depending on the current working phase of the suction/pressure unit of the first fluid system is disclosed.

19 Claims, 3 Drawing Sheets

(58) Field of Classification Search
    USPC .......................................................... 604/67
    See application file for complete search history.

(56) References Cited

U.S. PATENT DOCUMENTS

| | | | |
|---|---|---|---|
| 5,921,951 A | 7/1999 | Morris | |
| 7,083,719 B2* | 8/2006 | Bowman, Jr. ........... | A61M 1/28 210/143 |
| 8,323,007 B2 | 12/2012 | Butterfield | |
| 2005/0069425 A1 | 3/2005 | Gray et al. | |
| 2007/0166181 A1 | 7/2007 | Nilson | |
| 2010/0042068 A1 | 2/2010 | Friebe et al. | |
| 2011/0021993 A1 | 1/2011 | Bar-Haim et al. | |
| 2016/0015564 A1 | 1/2016 | Pang et al. | |
| 2016/0256627 A1 | 9/2016 | Gray et al. | |

FOREIGN PATENT DOCUMENTS

| | | |
|---|---|---|
| CN | 102202708 | 9/2011 |
| CN | 102512725 | 6/2012 |
| DE | 199 19 572 | 11/2000 |
| DE | 10 2010 005 746 | 7/2011 |
| DE | 10 2010 007 464 | 8/2011 |
| EP | 0191071 | 8/1986 |
| JP | 2010535310 A | 11/2010 |
| RU | 2325927 C2 | 6/2008 |
| WO | WO 86/01115 | 2/1986 |
| WO | WO 94/09847 | 5/1994 |
| WO | WO 01/21525 | 3/2001 |
| WO | WO 2006/000415 | 1/2006 |
| WO | 2009017487 A1 | 2/2009 |
| WO | WO 2009/017487 | 2/2009 |
| WO | WO 2009/026060 | 2/2009 |

OTHER PUBLICATIONS

German Search Report for DE 10 2012 113 087.63 dated Jul. 4, 2013.
"Membranpumpe"—Versionsunterschied, Dec. 8, 2012, Wikipedia with translation.
Chinese Office Action and Search Report, with translation, for CN201380067766.5 dated Sep. 23, 2016.
European Exam Report for EP 13 821 827.6 dated Aug. 18, 2015.
Japanese Office Action for Japanese Application No. 2015-548674, dated Oct. 3, 2017 with translation, 6 pages.
Russian Office Action for Russian Application No. 2015130618/14, dated Sep. 4, 2017, including English translation, 10 pages.
Decision of Rejection for Japanese Application No. 2015-548674, dated Jan. 23, 2018, including English translation, 6 pages.
Russian Office Action for Russian Application No. 2015130618/14, dated Feb. 2, 2018, including English translation, 8 pages.
Japanese Office Action, with translation, for JP2015-548674 dated Feb. 7, 2017.

* cited by examiner

PUMP FOR MEDICAL PURPOSES

CROSS REFERENCE TO RELATED APPLICATIONS

This application is the U.S. national phase application of PCT International Application No. PCT/EP2013/077950 filed Dec. 23, 2013, which claims priority to German Patent Application No. DE 10 2012 113 087.6 filed Dec. 24, 2012, the contents of each application being incorporated by reference herein.

FIELD OF THE INVENTION

The present invention relates to a medical pump for conveying fluids (liquids) with the best possible control of volume and pressure with simultaneous application of the principle of using disposable items for the flow elements.

BACKGROUND

In daily clinical practice, especially with the intensive medical treatment of patients, so-called infusion pumps are used for the continuous or short-interval administration of active agents. Usually, these are syringe pumps or volumetric pumps (e.g. hose pumps, peristaltic squeeze pumps, roller pumps, etc.). These two pump types are of fundamentally different nature in terms of the maximum selectable conveying rate, i.e., the highest possible volumetric flow, the maximum administrable total volume without changing the disposable article, the conveying profile and the accuracy (e.g. metering accuracy). In simplified terms, the following selection criteria apply to these pumps:

Syringe pumps are used for:
High demands concerning the precision of the volumetric flow (e.g. high metering precision over time and/or high uniformity of the conveyance),
high demands concerning the pressure profile (e.g. no pressure drops by "retraction phases", for example),
smaller volumetric flows,
high long-term consistency in the volumetric flow (e.g. no effects of ageing and/or fatigue processes, e.g. due to the milling of a plastic hose and/or no influence by the "creeping" of an amorphous plastic hose) and low application volume for each of the disposable articles (e.g. syringe).

Volumetric pumps are used for:
Lower demands concerning the precision of the volumetric flow (lower metering precision over time),
lower demands concerning the pressure profile (e.g. pressure variations due to "retraction phases"),
large volumetric flows,
lower long-term consistency and
enhanced application volume for each of the disposable articles (e.g. hose—e.g. employing a flow-based pumping principle allows to use any container (sizes) upstream the pump and to exchange them without changing the hose).

As a consequence, two different pump systems (according to different pumping methods) have been established in the marketplace with different (hitherto not combinable) performance profiles and hence different application situations.

Specifically, the syringe pump conceptually has a piston/cylinder assembly (forms and at the same time also limits the stored total volume) and moves the (syringe) piston in the (syringe) cylinder by motor power via e.g. a rotation-translation conversion gear, whereas the volumetric pump subdivides a hose segment by force effect (pump rotor with circumferentially spaced squeezing elements) in sequential, fluidically separate fluid chamber or partially closes them (also referred to as occlusion) and moves said occlusion e.g. periodically, for instance as a peristalsis, toward the pump output (i.e., toward the patient, for example).

DESCRIPTION OF THE RELATED ART

The prior art knows a multitude of different pump constructions both for the syringe pump and for the volumetric pump on the medical application sector.

A characteristic feature of the volumetric pump constructions is that fluids to be administered are taken in from separate fluid containers and then conveyed under pressure toward the patient, the required suction effect being generated in the main by the restoring ability (inherent elasticity) of the squeeze hose which is usually provided as a disposable article. Due to this fact, the volumetric flow significantly depends on the flow resistances in the pump inlet (suction side of the pump), the difference in the altitude between the container and the pump/suction mechanic system and the (basically variable) own dynamics of the hose material. On the other hand, the absolute accuracy with the same constructional and environmental conditions is basically limited by the accuracy of the hose material as such (thickness of the wall, inner diameter, composition/quality of the material, etc.). As the mechanical displacement of the closure means/the occlusion point represents a substantial mechanical stress for the employed hose material, the volumetric flow continuously changes over time as a result of effects in terms of wear and tear, fatigue, ageing and creeping in the hose material.

SUMMARY OF THE INVENTION

Therefore, there is a basic need of a type of medical universal pump in which the application advantages of the two pump types described above are combined in a single pump principle. This means that the medical universal pump is supposed to show an improved controllability in terms of the volumetric flow and the pressure profile corresponding to a syringe pump by a greater independence of influential variables of a volumetric pump known per se, such as
flow resistances in the fluidic system, in particular in the inlet, but also in the outlet,
geometry and material variations of the disposable article, variations of the own dynamics of the disposable article, effects in terms of wear and tear, fatigue, ageing and plastic creeping of the disposable articles,
pressure in the fluid system, in particular in front of and behind the pump segment, and ambient pressure,
device temperature, ambient temperature and fluid temperature. Further, the universal pump should be able to convey total volumes of any desired size without exchanging the disposable article comprising the pump segment—as it is possible with volumetric pumps for instance by exchanging e.g. an infusion bag without changing e.g. the infusion hose including the pump segment.

The present invention is thus based on an object to provide a medical pump in which the positive attributes of a syringe pump which are known per se are combined with positive attributes of a volumetric pump (squeezing pump/hose pump) known per se.

The basic principle of the medical (suction/pressure) pump according to the invention consists in arranging two separate hydraulic/pneumatic systems or hydraulic/pneumatic circuits. The first hydraulic (or pneumatic) system (circuit) serves as a primary energy source for providing a suction/pressure force and does not come into direct contact with the fluids which are to be administered to the patient (this is particularly advantageous as otherwise the pump would have to be cleaned and/or disinfected after or before use). This first system, being designed analogue to the syringe pump system and forming a sort of inner simulation circuit, is distinguished by a high precision in producing, measuring and/or controlling volumetric flows and pressures—"upstream" (in front of the pump segment), in the pump segment and/or "downstream" (after the pump segment). The second hydraulic (or pneumatic) system (circuit) serves as a secondary-energy source for drawing and conveying fluids to be administered to the patient and thus is designed as a disposable flow article (analogue to the volumetric pump principle) and comprises a disposable article with an inflow and an outflow. The second system (specifically, the disposable article of the second system) is actuated/operated via/through the first (reusable) system.

According to the invention, the first system is reusable and preferably directly coupled to the second system or its disposable article in such a manner that a change in volume in the first system results in a corresponding (possibly identical, but at least predictable and/or determinable change in volume in the second system (disposable article); by way of example, e.g. gas bubbles enclosed in the first or second system can be measured, considered and/or compensated on the basis of their compression curve. This is why the second system (disposable article) essentially receives the accuracy of the first system.

The first system may be a preferably pressure-proof fluid chamber (i.e., a negative or positive pressure existing in the fluid chamber remains essentially stable after reaching the state of equilibrium/alternatively: the pressure course is predictable) comprising at least one membrane or a membrane-like, movable and/or deformable wall. The coupling to the second system is effected via the membrane.

If the membrane of the first system rests, for instance, on the membrane (or membrane-like wall) of the second system in an essentially form-fitting manner, it will transmit any pressure changes in the first system to the second system e.g. in the form of a deformation and hence transfers e.g. an enlargement or reduction of the fluid chamber of the second system. It is particularly advantageous if the coupling between the first and second fluid chamber is constructed similar to a pressure load cell, i.e., the form-fit between the membranes is or can be achieved, supported and/or improved for instance by evacuating or filling the membrane interspaces and/or a space which surrounds the (joined) membranes and whose walls may consist for instance of walls belonging to the first system as well as walls belonging to the second system (and hence forms an evacuatable/fillable pressure load cell only if the disposable article of the second system is inserted in the reusable article of the first system). This means that the (firm) coupling between the first and second system is achieved by a (pressure-proof) fluid pressure chamber comprising two pressure chambers which are separated by at least one movable wall. This concept of coupling also offers e.g. the basic possibility that e.g. any elastic disposable article of any desired shape (e.g. a hose comprising a hose interior volume as the second pressure chamber) can be molded, with the volume of the first pressure chamber (as a part of the first system) being variable e.g. according to the syringe pump principle by the volume of the second pressure chamber being compressed and/or expanded through the first system. This means that the deformation of the second system (disposable article) may bring about a change in volume (increase/decrease) of the second pressure chamber. Thus, a suitable activation of the first system by the second system allows to draw in fluid from a container (expansion of the second pressure chamber by a reduction or displacement of the volume of the first pressure chamber or in the first pressure chamber) or to displace it (compression of the second pressure chamber by an increase or displacement of the volume of the first pressure chamber or in the first pressure chamber). Due to this characteristic, the method is also able according to the invention to empty syringes which are connected on the upstream side (as fluid containers which are typical for syringe pumps) and is also capable of emptying e.g. bottles or bags (as fluid containers which are typical for volumetric pumps) due to the suction characteristics being controlled by the first system (independently on the factors initially mentioned).

In more specific terms, the set problem is solved with a medical fluid pump comprising a first inner fluid system inter alia consisting of a motor-driven suction/pressure unit or volume displacement unit and a first fluid space which can be filled with fluid or can be emptied by the suction/pressure unit. In addition, the pump according to the invention comprises a second, external fluid system consisting of a second fluid pressure chamber which is coupled to the first fluid pressure chamber via a movable separating wall in a fluid-tight and pressure-proof manner and or volume-dynamic fashion and which is alternately connected to a suction line and pressure line via a valve means preferably of the second fluid system as a function of the current working phase of the suction/pressure unit of the first fluid system.

Thus, the actuation of the suction/pressure unit allows to vary the filling volume of the first fluid pressure chamber, this circumstance being correspondingly transferred via the movable separating wall to the second fluid pressure chamber. This means that also the second fluid pressure chamber will change its volume corresponding to the equalizing movement of the separating wall and hence draws in fluid from a supply container through the suction line and/or ejects fluid via the pressure line toward the patient. The precision in the adjustment of the volumetric flows occurring here is achieved essentially with the suction/pressure unit independently of the possibly varying properties of the material of e.g. the separating walls. At the same time, the fluid-tight division of the system in two pieces allows to design the external system or parts thereof as a disposable article. It is particularly advantageous that this measure allows to prevent any parts of the second system, for instance its separating wall, from coming into contact with fluid of the ("hydraulic") system. This allows to essentially do away with any additional operations such as e.g. the regular refill with fluid and/or the cleaning, which are required in case of such fluid contact. Further, the system can be advantageously designed as a system which is sealed off in the light of sterility, e.g. a disposable article system. This allows to eliminate additional operations such as a special disinfection or sterilization which would otherwise be required.

It is preferred that the first fluid system comprises a pressure sensor within the first pressure chamber and preferably a volume/mass flow sensor between the first pressure chamber and the suction/pressure unit for the controlling of the suction/pressure unit or the drive units thereof and/or a drive unit having such a high precision that such a volume flow sensor or mass flow sensor is not needed. A pressure sensor or a volume/mass flow sensor, and measures of control engineering as well, allow to use such suction/ pressure units (gear pumps, vane pumps, etc.) which due to their design do not reach the required precision or uniformity. To this end, an intermediate phase can be advantageously introduced, e.g. a phase during which both valves (upstream and downstream) are closed (if the valves are closed, it is possible to run a specific pressure in the systems such that there is a conveying profile (upstream and/or downstream) occurring after opening a respective valve which is particularly suitable for the application case).

By way of example, provision can be made that a fluid receiving body, being flexible at least in parts, is placed in the second fluid pressure chamber to be in contact with the movable separating wall of the first system, with the option that the fluid receiving body is fluidly connected to the valve means. In this case, for example, the container may be used again which forms the second fluid pressure chamber, as it is not contaminated with the fluid in the second fluid system; here, it is only necessary to dispose of the separately insertable fluid receiving body (for example a hose or bag).

Another aspect of the present invention relates to that very fluid (receiving) container of the medical fluid pump according to the invention comprising at least one flexible outer wall which closes the fluid container in a fluid-tight manner at least in the assembled state and which may be made to contact the movable separating wall.

According to a preferred aspect of the invention, provision is made that the medical fluid conveying device is constructed such that a pressure sensor in the first fluid system as a simulation circuit allows, at least essentially, to determine the pressure in the second fluid space of the second fluid system and in the system connected on the upstream and/or downstream side.

According to a further preferred aspect of the invention, provision is made that the pressure sensor in the first fluid system also allows, at least essentially, to determine at least one contribution of one and/or both separating walls to the pressure in one and/or both fluid spaces.

According to a further preferred aspect of the invention, provision is made that an intermediate phase may be achieved between a suction phase and a displacement phase and/or between a displacement phase and a suction phase; in said intermediate phase, the upstream valve as well as the downstream valve is closed.

According to a further preferred aspect of the invention, provision is made that, at least essentially, the volume can be determined which has been added to the first fluid space in a certain period of time or has been withdrawn from it.

According to a further preferred aspect of the invention, provision is made that the fluid volume added to the fluid space or withdrawn from it during a period of time can be derived (at least essentially) from signals existing in this period of time on the part of the pumping unit and/or a sensor system—such as e.g. a volume and/or mass flow sensor—coupled to the pumping unit.

According to a further preferred aspect of the invention, provision is made that a desired pressure can be controllably set (at least essentially) in the second fluid space during an intermediate phase.

According to a further aspect of the invention, it is preferably provided that a specific pressure, generated during an intermediate phase in the second fluid space, has an advantageous effect on the subsequent suction and/or displacement phase and/or on the upstream and/or downstream pressure profile.

According to a further preferred aspect of the invention, provision is made that a particularly uniform pressure profile can be achieved on the upstream and/or downstream side.

According to a further preferred aspect of the invention, provision is made that two or more tuples ("fluid volume in the first fluid space", "pressure at the pressure sensor") or the like (e.g. piston position and pressure) can be determined in the intermediate phase.

According to a further preferred aspect of the invention, provision is made that the tuples determined e.g. in the intermediate phases can be utilized to determine the consistency and/or ageing of one of both separating walls and/or the tightness of the system and/or the tightness of one and/or both closed valve means and/or the compliance of the system and/or the compression behavior of the fluids in the systems and/or the upstream and/or downstream pressure and/or the correlation between the fluid volume in the fluid spaces and the contribution of one or both separating wall deflections or deformations to the pressure signal at the pressure sensor and/or the like.

According to a further preferred aspect of the invention, provision is made that the compression behavior at least basically allows to determine the ratio between the gaseous and liquid phase in one of the two and/or in both fluid spaces.

According to a further preferred aspect of the invention, provision is made that gas bubbles stuck in the second fluid chamber, e.g. with specific valve positions, can be moved into the downstream and/or upstream systems e.g. by pressure pulses in the first system.

According to a further preferred aspect of the invention, provision is made that the pressure profile resulting at the upstream and/or downstream side have a beneficial effect on the degassing and/or agglomeration of gas in the fluid of the second system or in a system connected to said system.

According to a further preferred aspect of the invention, provision is made that any failures in the systems which are connected upstream and/or downstream, such as occlusions of a line and/or leaks, can be detected on the basis of the pressure profile in the suction and displacement phases.

According to a further preferred aspect of the invention, provision is made that undesired variations (e.g. pressure variations) due to e.g. the altitude changes of parts of the systems connected upstream and/or downstream can be compensated.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1A:
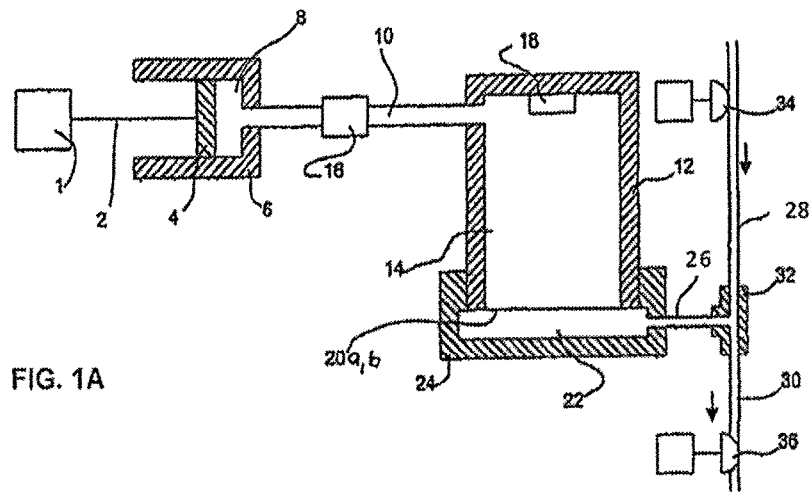
FIGS. 1A, 1B, and 1C show the functional principle of a medical pump according to the present invention on the basis of three respective operational positions.

According to FIG. 1A, the basic principle of the pump according to the invention (universal pump) provides a drive unit 1 (such as an electric motor or similar power source), which is in operative connection to a translation piston 4 via a force transmission unit 2, said translation piston in turn being supported in a suction-/pressure cylinder 6 to define a fluid chamber 8 with a variable volume. This cylinder-fluid chamber 8 is connected to a first fluid container 12 via a first fluid line 10; a first pressure chamber 14 is formed in the first fluid container and the first fluid line 10 opens into it. The fluid chamber 8, the fluid line 10 and the first pressure chamber 14 may also be, for instance, a contiguous volume in which the division into a fluid chamber, a fluid line and a pressure chamber is merely virtual and can be chosen at will, so to speak, and only serves the purpose of a better functional descriptability.

By way of example, a volumetric flow sensor 16 may be provided in the first fluid line 10 and a pressure sensor 18 may be provided in the first pressure chamber 14. The piston-/cylinder unit 4, 6, the first fluid line 10 and the first pressure chamber 14 (or first container 12) together with the sensors 16, 18 and the drive unit 1 define a first hydraulic system S1. It is particularly advantageous if the first hydraulic system S1 is part of a reusable article such as an infusion pump, for example.

The first pressure chamber 14 is closed with a first separating wall 20a, which may be movable and/or deformable, e.g., for instance a membrane or a membrane-like device—it is particularly advantageous if the other walls of the hydraulic system S1 are rigid, so that a pressure increase or decrease in the pressure chamber only causes a deformation of the separating wall 20a, provided that the separating wall 20a is not prevented from being deformed, for example by a mechanical intervention from outside.

A second hydraulic system S2 is defined by a second pressure chamber 22 within a second container 24 which can be mounted or is mounted to the first fluid container 12 or can be inserted or is inserted in the first fluid container 12.

It is particularly advantageous if the second hydraulic system S2 is part of a disposable article, for instance an infusion set. In the exemplary embodiment, the disposable article may include, for instance, a second fluid line 26, a Y-piece 32, a suction line 28 and a pressure line 30, and the valves 34 and 36 may be a reusable article, as will be described below.

According to this exemplary embodiment (but not absolutely necessary), the second pressure chamber 22 is closed by a second separating wall 20b, which may be similarly movable and/or deformable, such as a membrane or a membrane-like device.

Further, the second pressure chamber 22 is connected or can be connected to a suction line 28 and a pressure line 30 via a second fluid line 26. By way of example, the second fluid line 26 opens into a T- or Y-piece 32 connecting the suction line 28 to the pressure line 30, and a valve (such as a check valve or an electrically driven 2/2-directional switching valve or e.g. a hose segment or the like which can be squeezed off by an actuator applicable from outside) 34, 36 can be arranged or is arranged on and/or in the suction line 28 and pressure line 30. It is particularly advantageous if these are active valves, i.e., ones which are controlled in such a manner that e.g. a desired flow is produced in the desired direction, for instance from a fluid supply reservoir or container or tank (not shown in further detail) such as an infusion bag (pump suction side) towards a destination (not further shown), for instance a patient (pump pressure side). As an alternative to this, other valve constructions are also conceivable, such as a switching valve for selectively/alternately connecting the second fluid line 26 to the suction line 28 and pressure line 30.

It is particularly advantageous if the first separating wall 20a can be coupled to the second separating wall 20b in a mechanically reversible manner, e.g. in such a manner that both e.g. membranes can be joined essentially without any gap and the separating wall 20b (for instance in regard to the gap occurring between the membranes during/due to the deformation at elevated pressures in the pressure chambers 14 and 22) follows the motions/deformations of the separating wall 20a.

The functional principle of the pump according to aspects of the invention comprising the conceptual construction described above can be outlined as follows:

In the resting condition according to FIG. 1A, the volumetric flow in the second system S2 towards e.g. the patient (pressure side) is cut off because of the closed position of the downstream valve 36. At the beginning, the pressure chamber (fluid space) 22 is filled with a liquid and/or a gas and can be degassed initially. In the course of the further description, an essentially degassed second system S2 filled with liquid is assumed for reasons of simplification. In this state, the second movable wall, for example a membrane, is in its (e.g. unloaded) design situation, for instance. The first system S1 is also filled with a liquid and/or a gas. It is particularly advantageous if the fluid in S1 is an essentially incompressible medium or a medium with a defined and known compressibility curve. At that time, the piston 4 may be situated for instance in an advanced position with a small volume within the cylinder chamber 8. The first system S1, for example, may be essentially at atmospheric pressure in the resting condition.

Figure 1B:
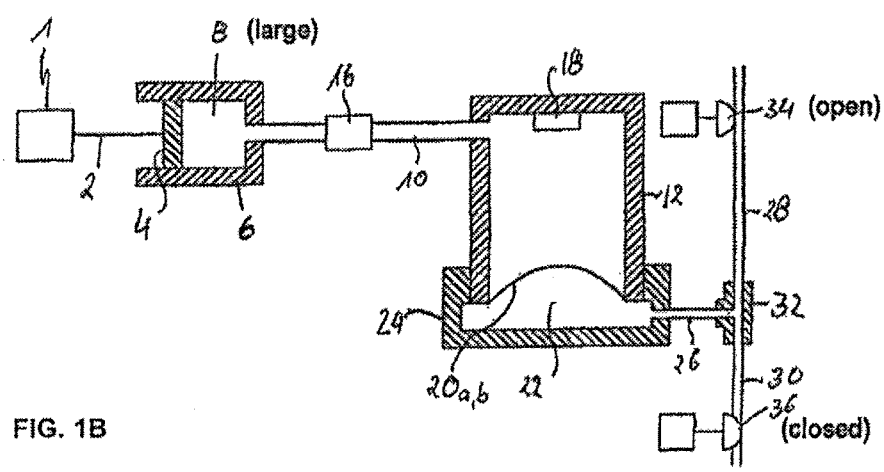

FIG. 1B, shows a suction state of the pump according to aspects of the invention. In this state, the piston 4 has been retracted by the drive unit 1 or is about to be retracted by it; thus, the volume of the cylinder chamber 8 is increased. As a result of this retraction movement of the piston 4, fluid flows out of the first fluid space 14 and through the first fluid line 10 into the cylinder chamber 8, with the option that the volumetric flow may be detected by a sensor 16.

The withdrawal of liquid out of the first pressure chamber 14 is compensated for by a corresponding movement of the separating wall 20a to reduce the volume of the first pressure chamber 14. Due to the separating walls 20a and 20b being coupled to each other, the separating wall 20b follows the movement of the separating wall 20a; at the same time, the volume of the second pressure chamber 22 enlarges in corresponding manner (e.g. in a particularly advantageous manner by the same amount of volume). As a result and corresponding to the volume enlargement movement of the separating wall 20b, a fluid is sucked into the second pressure chamber 22 from a (not shown) supply tank via the suction line 28 and the opened suction valve 34. The valve 36 continues to be closed in this (suction) phase, as illustrated in FIG. 1B.

The movement of the piston 4 may be designed via the cross-sectional surface area of the piston so as to be directly proportional to the volumetric flow through the first fluid line 10. This volumetric flow can be detected via the sensor 16 and/or determined, for instance, by the measurement of the rotational speed and/or the path on the piston 4, the force transmission unit 2 and/or the drive unit 1. Advantageously, it would also be conceivable that e.g. the rotational speed of the drive unit or the step number of a step motor establishes a precise reference to the volumetric flow.

As the retraction movement of the piston corresponds to the intake of liquid, the reduced pressure occurring in the first system S1 causes a deformation of the separating wall 20b of the second system S2 to the inside toward the first pressure chamber 14. Here, the sensor 18 is able to detect the generated reduced pressure and, for instance, also check the tightness of the systems S1 and S2 and of the valves 34 and 36, as well as the compressibilities or compliances of the above-mentioned components or of their fluids and also e.g. the (correctness of the) joining of the separating walls 20a and 20b in the light of expectations. The same applies to the forward movement of the piston. It is particularly advantageous that intermediate states (which are not shown here) such as the specific forward/rearward movement of the piston—with the valves 34 and 36 being in the closed state—can be used for generating a pressure increase or pressure decrease for determining the tightnesses, compressibilities and/or compliances of the (in particular above-mentioned) components of the pump according to aspects of the invention (advantageously a reusable pump) or of the associated article of the invention (advantageously a disposable article). This also offers e.g. the possibility to advantageously detect and/or measure air bubbles in the respective fluids (in other respects, the fluids may be essentially incompressible) and the like. It is also possible to detect and/or measure leakages, e.g. due to cracks in the separating walls. Similarly, any downstream or upstream occlusions of the lines can be detected with the corresponding valve positions, too.

Due to the pressure-proof/fluid-tight coupling between the pressure chamber 14 of the first system S1 and the pressure chamber 22 of the second system S2, the volume of fluid flowing into the pressure chamber 22 is exactly the same as the volume which is moved (sucked) from the piston 4 into the cylinder chamber 8.

Figure 1C:
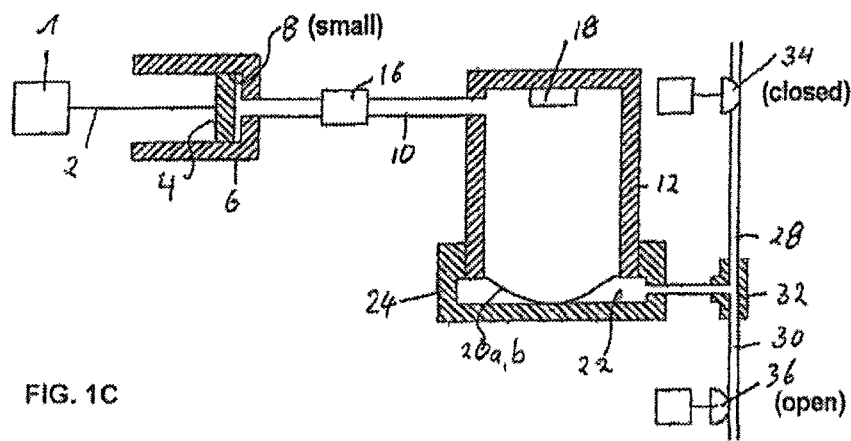

According to FIG. 1C, the piston 4 moves in the direction which is opposite to that in FIG. 1B, reducing the volume of the cylinder chamber 8 and, in doing so, squeezes a corresponding amount of fluid out of the cylinder chamber 8 and into the first pressure chamber 14. This results in a movement or deformation of the separating walls 20a and 20b towards the second pressure chamber (fluid space) 22 and a resulting displacement of fluid out of the pressure chamber 22.

In this (pressure) phase, the suction valve 34 is already closed; instead, the pressure valve 36 is opened, so that there will be a defined volumetric flow of fluid out of the second pressure chamber 22 and through the pressure line 30 toward the patient. This volumetric flow corresponds to the displaced (squeezed out) volume in the piston/cylinder unit 4, 6.

Depending on the movability (elasticity) of the separating walls 20a and 20b (e.g. membranes), fluid pressures build up in the first pressure chamber 14 which are superimposed by the pressures existing in the second system S2. If the pump is e.g. in the resting condition (according to FIG. 1A), e.g. the pressure sensor 18 is capable of detecting the pressure in the first system S1. Thus, any pressure changes or pulsations in the first system S1 are directly transferred to the second system S2 and vice versa. With a suitable design of the separating walls 20a and 20b (e.g., membranes), for instance with high flexibility along with low restoring forces and e.g. with low compressibility, it is also possible to determine any changes in the systems connected to the suction line 28 or pressure line 30, depending on the valve position of the valves 34 and 36. By way of example, such changes could be an ever increasing negative pressure on the upstream side for instance in the case of a connected (and not vented) infusion glass bottle and an ever increasing positive pressure on the downstream side for instance in the case of a connected and clogged infusion filter.

Due to the pressure-dynamic coupling of the two systems S1 and S2 according to the foregoing description (of the movable separating walls), the sensor 18 is also able to detect/determine any pressure changes which occur e.g. during the pumping phase both in the pump inlet (suction side) and in the pump outlet (patient side). In this way, it is also possible to detect e.g. any flow resistances in the downstream branch as well as in the upstream branch (which are caused, for example, by obstructions of any kind, filters, closed roller clamps, kinked hoses, etc.).

It is particularly advantageous that measuring or determining the respective pressure in the first pressure chamber 14 (or in the first hydraulic system S1), in the second pressure chamber 22 (or in the second hydraulic system S2), in the system hydraulically connected to the suction line 28 on the upstream side and in the system hydraulically connected to the pressure line 30 on the downstream side are improved if the contribution of the separating walls/membranes 20a and 20b, which falsifies the associated pressure signal e.g. on the pressure sensor 18 and may arise from e.g. the pretensions of said separating walls/membranes 20a and 20b and/or for instance from the restoring force counteracting the respective motion or deformation of the separating walls/membranes 20a and 20b, is determined and taken into consideration.

The determination of this contribution e.g. at a given first position z1 of the translation piston 4 may proceed, for instance, as follows (illustrated in idealized and simplified manner and only of exemplary illustrative character):

1.) Measuring the pressure signal on the pressure sensor 18, for instance, with opened valve 34 (upstream) and closed valve 36 (downstream), the measured value being designated in the following with Pu 2.) Measuring the pressure signal on the pressure sensor 18, for instance, with closed valve 34 (upstream) and closed valve 36 (downstream), the measured value being designated in the following with Pc 3.) Measuring the pressure signal on the pressure sensor 18, for instance, with closed valve 34 (upstream) and opened valve 36 (downstream), the measured value being designated in the following with Pd In a somewhat simplified manner, the following is true:

1.) Pu(z1)=Psurroundings+Pupstream+Pmembrane contribution(z1)

2.) Pc(z1)=Psurroundings+Pmembrane contribution(z1)

3.) Pd(z1)=Psurroundings+Pdownstream+Pmembrane contribution(z1)

Hence, Pupstream=Pu(z1)−Pc(z1) and Pdownstream=Pd(z1)−Pc(z1) can be determined.

If a further analogue measurement at a second piston position z2 is used in addition, it is possible to determine, e.g. with Pu(z1)−Pu(z2)=Pmembrane contribution(z1)−Pmembrane contribution(z2), for example also the difference in the contributions of the membranes to the pressure signal at the two piston positions z1 and z2.

It is not important if the equations adopted here represent a correct description of a real system (that depends specifically on further factors such as their compliances, the order of switching the valves and the time behavior thereof and the time behavior of the remaining system, etc.)—it is only important that the measuring of the pressure signal e.g. on the pressure sensor 18 with different valve constellations and possibly in different positions of the piston 4 (or of the membranes) allows to establish so many equations that there are more equations than unknown factors—that the equations can be solved therefore and the unknown factors existing in the equations (e.g. environmental pressure, upstream pressure in the system, membrane restoring force at a certain position*surface area, downstream pressure in the system, etc.) can be determined.

It goes without saying that the fourth valve constellation (both valves are opened) can be used as well.

Such or similar measurements may also be used, for example, to "calibrate" the reusable article separating wall/membrane 20a for instance during production and/or during a device service (inspection, self-calibration, self-test, etc.)—that is to say to measure its behavior and to store it (e.g. in permanent fashion) for instance in the reusable article (e.g. in the infusion pump).

Such or similar measurements may also be used, for example, to make an initial "calibration" of the disposable article separating wall/membrane 20b e.g. prior to the commencement of the conveyance (e.g. before the infusion start e.g. after inserting the disposable article in the infusion pump)—that is to say to measure its behavior and to deposit the latter for instance in the reusable article (e.g. in the infusion pump) (e.g. only temporarily over the time duration of the application of this disposable article).

Such or similar measurements may also be carried out, for example, during operation—here, it is advantageously possible to introduce intermediate phases (which are not shown here) e.g. between the suction phase (FIG. 1B—corresponds to Pu) and the displacement phase (FIG. 1C—corresponds to Pd), which may correspond to Pc, for instance. Further, the piston may also be moved forward and/or rearward in these intermediate phases, in order to be able to use measurements at different piston positions for the determination of a variable.

It is also particularly advantageous that any pressure differences between S1, S2 and the systems connected to S2 in the upstream and downstream branches are equalized by a corresponding travel of the piston 4 e.g. during such intermediate phases e.g. with closed valves 34 and 36—these and similar procedures allow to establish a very uniform hydraulic pressure profile in all the mentioned hydraulic branches, in particular upstream and downstream. Thus, a very uniform conveyance profile can be achieved as well. Further, such a proceeding increases the achievable precision by a significant extent. In addition, uniform pressure profiles reduce the degassing in fluids and/or the agglomeration of micro-bubbles to macro-bubbles.

It is particularly advantageous that virtually all of the variables which are of interest for the pumping action can be checked and controlled with one single pressure sensor 18 and two valves 34 and 36.

A great benefit is also represented by the possibility to detect and/or compensate a possible alteration of e.g. the membrane performance (e.g. due to material fatigue and/or defect)—before the start, during the conveyance and/or after the end of the conveyance. Thus, such approaches allow comprehensive self-tests as well.

Examples for detectable system changes are the following: the height level change of the upstream fluid source or of the downstream fluid sink and/or of the reusable article or the like, changes in the flow resistances e.g. upstream and/or downstream (and thus e.g. line occlusions and/or leakages), counter pressures e.g. downstream (e.g. also the patient's blood pressure or the like), leaks in the first and/or second hydraulic system, material fatigues and/or—defects such as e.g. cracks and/or holes or the like in the separating walls 20a and/or 20b, but also e.g. alterations of the fluids (e.g. due to a new composition of the infusion liquid and/or due to e.g. air bubbles e.g. in S1 and/or in S2). On the other hand, the plausibility of the pressure sensor signal can also be checked and with this the functionality of the pressure sensor.

Subsequent to the pumping or displacement phase according to FIG. 1C, the pump again changes to the suction phase according to FIG. 1B, with the phase change between suction and displacement being repeated preferably continuously or in intervals. In particular in case of the continuous repetition, a discontinuous volumetric flow can be reduced or largely avoided here in that the intrinsic dead phases which may have a disturbing effect in particular on the downstream side (on the pump pressure side) are minimized by different motion speeds of the piston 4 (high suction speed/low displacement speed). Further, the principle may also be expanded such that during a dead phase ("retraction phase", "loading phase", "suction phase") a second pump according to aspects of the invention performs the transport work and vice versa (so to speak a dual or two piston pump).

As can be also taken from FIGS. 1A-C, it appears to be advantageous to implement at least the second fluid container 24 including the separating wall 20b as a separate component, in particular as a disposable article, with preferably the entire second system S2 being provided as a disposable article. This means that in this case the second container 24 may be coupled to the first container 12 in separable fashion (e.g. in reversible fashion) in such a manner that a pressure change in the first pressure chamber 14 results in a compensatory movement of the separating wall 20a and 20b and thus in a change in volume of the second pressure chamber 22.

By way of example, both containers may be plugged into each other and/or screwed and/or pressed to each other. The containers may be flanged to each other as well. Owing to the provided two e.g. parallel separating walls/membranes which each seal off the first and the second pressure chamber, respectively, it is not necessary to empty the pressure chambers during dismantling the two containers.

In the following, technical references to specific technical implementations of the afore-mentioned pump principle will be given on the basis of FIGS. 2A-B, and 3A-C.

Especially if the conveying process is to take place under sterile conditions, it may also be advantageous if the concept of a disposable article does not relate to the entire second system S2 including the container 24, but is reduced e.g. to elements which are specifically adapted to the second container and, so to speak, form a lining of said container.

Figure 2A:
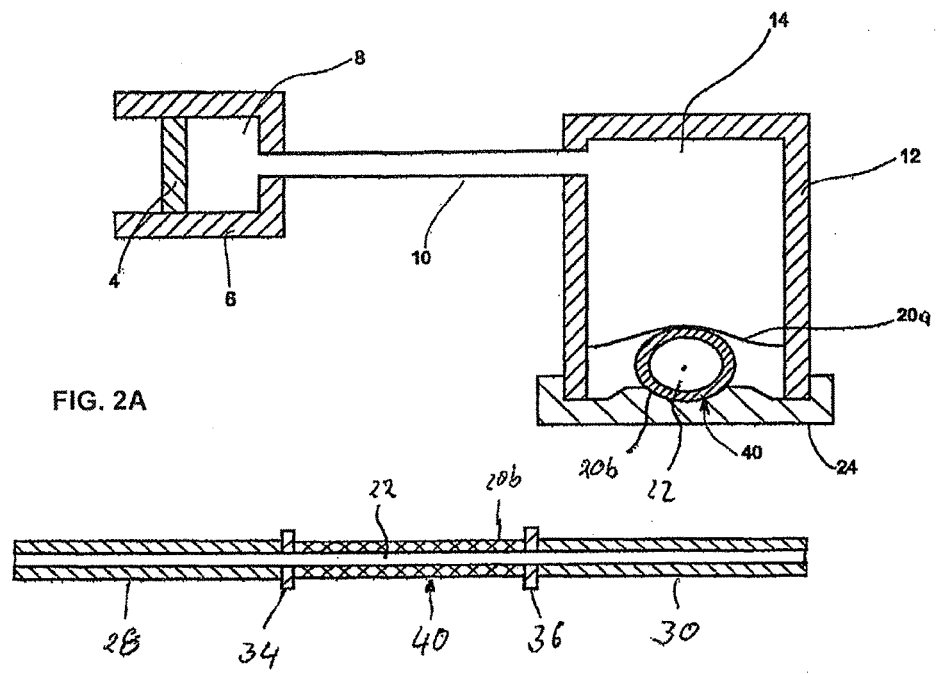
FIGS. 2A and 2B show, on the basis of two respective operational positions, a first preferred exemplary embodiment of a medical pump according to the functional principle of FIGS. 1A-C using a standardized disposable article, for instance an (infusion) hose.
Figure 2B:
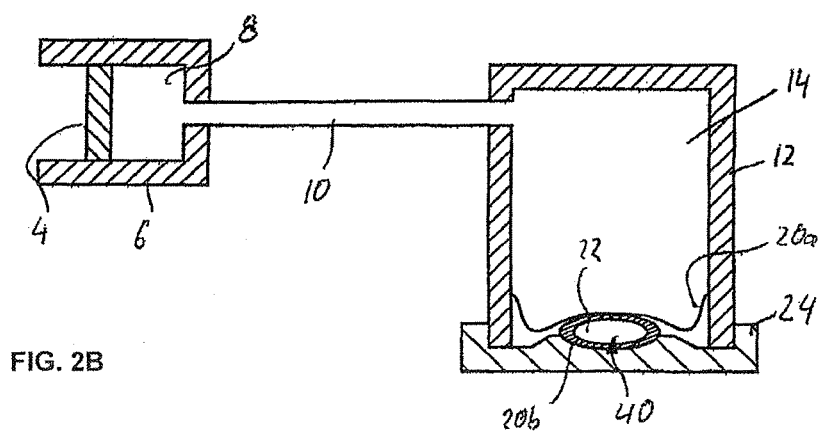

According to FIGS. 2A-B, the actual second fluid pressure chamber is formed so to speak by e.g. an (e.g. infusion) hose 40 as a fluid receiving body which can be inserted in the second container 24 and is coupled to the separating wall/membrane 20a in a form-fitting manner. This means that the wall of the hose 40 corresponds to the second separating wall/membrane 20b; in case the material of the hose is sufficiently flexible/deformable, the separating wall 20a is able to deform the hose 40 in a corresponding fashion, so that an e.g. directly proportional volumetric flow can be produced. For this reason, it is only necessary to implement the hose 40 (for instance along with the suction/pressure lines 28, 30 connected thereto and possibly also the valves 34, 36) as a disposable article.

Figure 3A:
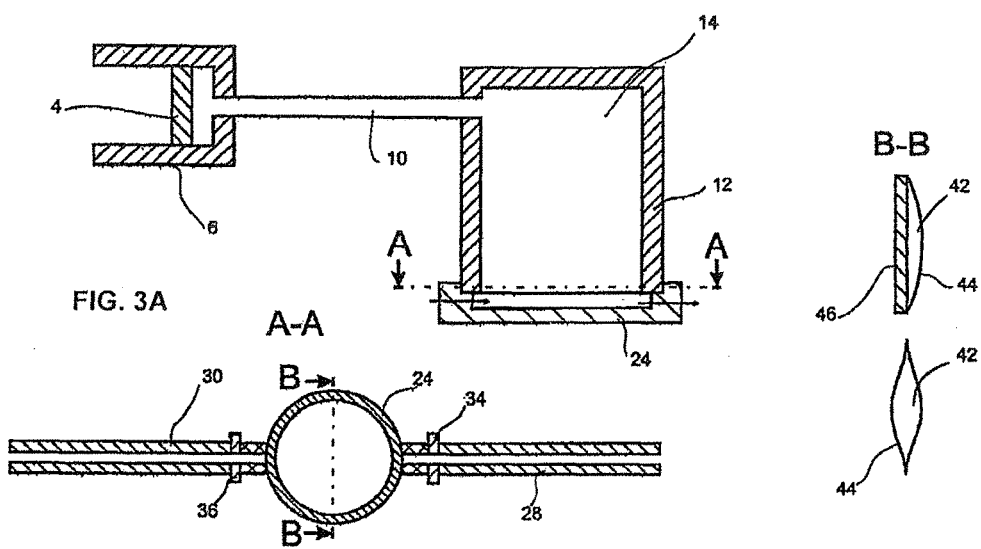
FIGS. 3A, 3B, and 3C show, on the basis of two operational positions, a second preferred exemplary embodiment of a medical pump according to the functional principle of FIGS. 1A-C using an exemplary specific disposable article which is particularly advantageous.
Figure 3B:
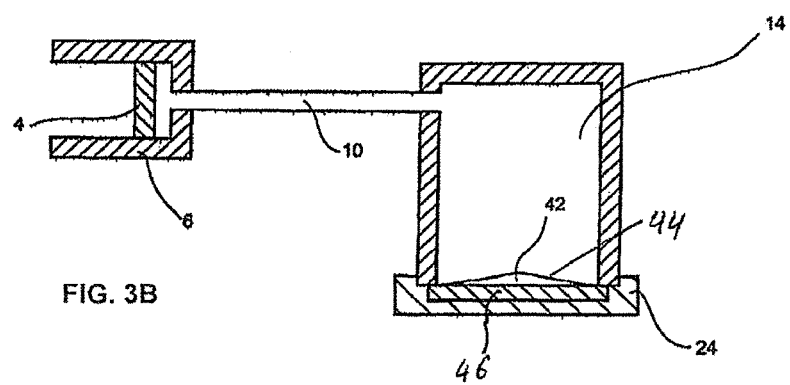
Figure 3C:
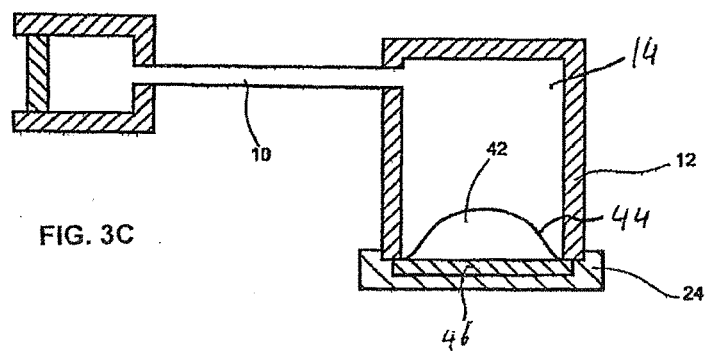

As an alternative and by way of example, provision is made according to FIGS. 3A-C to (e.g. loosely) place e.g. a cushion-like inlay 42 in the second container 24. In the position predefined by design (e.g. pressure-less), the e.g. bag-shaped cushion 42 may have the same volume as the second container (fills it essentially completely) and may consist of e.g. a flexible/elastic foil/membrane 44 which has its edge fixed to e.g. a plate 46 in a fluid-tight manner (advantageously, it is also possible that the disposable article already covers the function of the second container 24—for instance by its housing being able to be mounted to the first container 12 in a fixed and/or reversible and/or tight fashion—with the advantage, for example, that an additional component for the second container 24 is not required). At least one opening (not further specified) for the second fluid line 26 opens into the bag's inner space (second pressure chamber) formed in this way. This opening may be recessed in the plate 46, for example. It is also possible, however, to provide two or more entries, e.g. one for the supply line 28 and one for the discharge line 30. In this context, it is referred to the fact that—instead of using the plate 46—the bag can be exclusively made of the flexible material. With this embodiment, the movement or deformation of the separating wall 20a is directly transferred to the bag 42 which undergoes a corresponding change in volume.

The exemplary embodiments described above have been selected such that the mode of functioning of the pump according to aspects of the invention can be demonstrated in a simple way. Thus, they do not necessarily correspond to a real form of implementation. By way of example, the piston/cylinder unit illustrated in the form of separate parts may already be a constituent of the first container. It is also conceivable that the piston of the piston/cylinder unit fills two or more first systems with liquid or empties them, and a second system can be connected or is connected to said systems in each case. This makes sense, for example, if the dead phases in the previously described exemplary embodiment with a single system are to be minimized by using several systems connected in parallel (with a corresponding phase shift).

It should also be noted that the piston/cylinder unit only represents an exemplary solution. It is also conceivable that any possible pumping method can be applied, such as a swash plate pump, a vane pump, a gear pump, etc. Such pumping units which per se do not allow a sufficient volumetric flow precision (membrane pumps, etc.) may be equipped according to aspects of the invention e.g. with a volumetric flow sensor and/or a mass flow sensor or the like, to bring about the desired accuracy by control technology.

The invention claimed is:

1. A medical fluid conveyor device, comprising:
    a first fluid system including:
        a motor-driven pumping unit,
        a first fluid container,
        a first fluid line connecting the motor-driven pumping unit to the first fluid container, wherein the pumping unit delivers fluid to and removes fluid from the first fluid container via the first fluid line, and
        a first separating wall which closes the first fluid container,
    a second fluid system which couples to the first fluid system and includes:
        a second fluid container, and
        a second separating wall which closes the second fluid container and couples to the first separating wall in such a manner that a change in pressure in the first fluid container has an impact on the pressure in the second fluid container;
    at least one pressure sensor located within the first fluid container; and
    a fluid receiving body which is flexible at least in portions and which can be inserted in the second fluid container to form the second separating wall which is in contact with the first separating wall and to which a valve is fluidically connected, wherein the flexible fluid receiving body is a medical hose or a bag which is flexible at least in parts;
    wherein the medical fluid conveyor device is configured to derive the fluid volume added to or withdrawn from at least one of the first fluid space or the second fluid space based on signals from at least one of the motor-driven pumping unit or a sensor system coupled to the motor-driven pumping unit.

2. The medical fluid conveyor device according to claim 1, further comprising:
    at least one suction line which is connected to the second fluid container and comprises an associated valve and
    at least one pressure line which is connected to the second fluid container and comprises an associated valve,
    wherein the first fluid system is configured to generate, determine, and control at least one of a volumetric flow or a mass flow from the suction line into the pressure line of the second fluid system, and at least one of a volumetric flow or a mass flow from the pressure line into the suction line of the second fluid system.

3. The medical fluid conveyor device according to claim 1, wherein in the event of an opened upstream valve and a closed downstream valve, a reduction of the fluid volume in the first fluid container by a change in volume ($\Delta V$) results in a corresponding enlargement of the fluid volume in the second fluid container by the change in volume ($\Delta V$), the change in volume ($\Delta V$) being taken from a fluid system connected to a suction line at an upstream point.

4. The medical fluid conveyor device according to claim 1, wherein in the event of a closed upstream valve and an opened downstream valve, an enlargement of the fluid volume in the first fluid container by a change in volume ($\Delta V$) results in a corresponding reduction of the fluid volume in the second fluid container by the change in volume ($\Delta V$), the change in volume ($\Delta V$) being essentially added to a fluid system connected to a pressure line at a downstream point.

5. The medical fluid conveyor device according to claim 1, wherein the at least one pressure sensor is hydraulically connected to the first fluid container.

6. The medical fluid conveyor device according to claim 1, further comprising:
    at least one of a volumetric flow sensor or mass flow sensor in the first fluid system, said at least one sensor allowing to determine the fluid volume which is added to or removed from the first fluid container during a period of time.

7. The medical fluid conveyor device according to claim 1, wherein the first fluid container and the second fluid container are mechanically connected at the first and second separating walls.

8. The medical fluid conveyor device according to claim 1, wherein the second system in its entirety is designed as a disposable item or in that at least those components of the second system are designed as disposable items which are directly in contact with the fluid.

9. The medical fluid conveyor device according to claim 1, wherein coupling of the first and second separating walls is at least one of effected, supported, maintained, improved, checked or unloosened by checking and controlling the pressure in a separating wall interspace which is also delimited at least by partial areas of the first and second separating walls.

10. The medical fluid device of claim 1, wherein the first and second separating walls are membranes.

11. The medical fluid conveyor device according to claim 1, wherein the at least one pressure sensor is pneumatically connected to the first fluid container.

12. The medical fluid device of claim 1, wherein the first separating wall is movable.

13. The medical fluid device of claim 12, wherein the second separating wall is movable.

14. The medical fluid device of claim 12, wherein the second separating wall is deformable.

15. The medical fluid device of claim 1, wherein the first separating wall is deformable.

16. The medical fluid device of claim 15, wherein the second separating wall is movable.

17. The medical fluid device of claim 15, wherein the second separating wall is deformable.

18. The medical fluid device of claim 1, wherein the second separating wall is movable.

19. The medical fluid device of claim 1, wherein the second separating wall is deformable.

* * * * *